United States Patent
Mitsuno et al.

(10) Patent No.: US 10,022,936 B2
(45) Date of Patent: Jul. 17, 2018

(54) COMPOSITE SHEET AND METHOD FOR MANUFACTURING THE SAME

(71) Applicant: UNICHARM CORPORATION, Ehime (JP)

(72) Inventors: Satoshi Mitsuno, Kagawa (JP); Jun Okuda, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 15/884,943

(22) Filed: Jan. 31, 2018

(65) Prior Publication Data

US 2018/0154607 A1    Jun. 7, 2018

Related U.S. Application Data

(62) Division of application No. 14/397,291, filed as application No. PCT/JP2013/062338 on Apr. 26, 2013.

(30) Foreign Application Priority Data

Apr. 27, 2012   (JP) ................. 2012-103908

(51) Int. Cl.
   *B32B 5/00*    (2006.01)
   *B32B 3/00*    (2006.01)
   (Continued)

(52) U.S. Cl.
   CPC .......... *B32B 5/26* (2013.01); *A61F 13/15699* (2013.01); *B29C 65/08* (2013.01);
   (Continued)

(58) Field of Classification Search
   CPC .... B32B 5/00; B32B 5/20; B32B 5/26; B32B 65/00; B32B 65/08; B32B 3/00;
   (Continued)

(56) References Cited

U.S. PATENT DOCUMENTS

| 5,707,710 A | 1/1998 | Zafiroglu |
| 7,741,235 B2 | 6/2010 | Hashimoto et al. |

(Continued)

FOREIGN PATENT DOCUMENTS

| JP | 2002-013056 A | 1/2002 |
| JP | 2002-067119 A | 3/2002 |

(Continued)

OTHER PUBLICATIONS

International Search Report from corresponding PCT application No. PCT/JP2013/062338 dated Aug. 6, 2013 (4 pgs).

*Primary Examiner* — Jacob T Minskey
*Assistant Examiner* — Matthew Hoover
(74) *Attorney, Agent, or Firm* — Brinks Gilson & Lione

(57) ABSTRACT

A composite sheet having an elastic layer and an inelastic layer and high breathability and a method for manufacturing such improved composite sheet. The composite sheet includes an elastic layer and an inelastic layer joined and laminated through a plurality of joints. The elastic layer is formed with first depressions overlapping the joints and extending in a transverse direction and first protrusions. Interior space if the first protrusions is filled with constituent fibers of the elastic layer. The inelastic layer is formed with second depressions overlapping the joints and extending in a longitudinal direction and second protrusions. Along the second depressions, the elastic layer and the inelastic layer come in contact with each other at the joints and, along the second protrusions, the inelastic layer is spaced from the elastic layer to define clearance gaps in these layers.

3 Claims, 6 Drawing Sheets

(51) Int. Cl.

| | | |
|---|---|---|
| *A61F 13/00* | (2006.01) | |
| *B32B 7/00* | (2006.01) | |
| *B32B 37/00* | (2006.01) | |
| *B32B 38/00* | (2006.01) | |
| *D04H 1/00* | (2006.01) | |
| *B32B 5/26* | (2006.01) | |
| *B32B 3/30* | (2006.01) | |
| *B32B 7/08* | (2006.01) | |
| *B32B 5/04* | (2006.01) | |
| *B32B 5/02* | (2006.01) | |
| *A61F 13/15* | (2006.01) | |
| *B29C 65/08* | (2006.01) | |
| *B32B 37/14* | (2006.01) | |
| *D04H 1/559* | (2012.01) | |
| *D04H 1/4374* | (2012.01) | |
| *B32B 7/02* | (2006.01) | |
| *B29L 31/48* | (2006.01) | |
| *B29L 9/00* | (2006.01) | |

(52) U.S. Cl.
CPC .............. *B32B 3/30* (2013.01); *B32B 5/022* (2013.01); *B32B 5/04* (2013.01); *B32B 7/02* (2013.01); *B32B 7/08* (2013.01); *B32B 37/0084* (2013.01); *B32B 37/144* (2013.01); *B32B 38/0012* (2013.01); *B32B 38/1875* (2013.01); *D04H 1/4374* (2013.01); *D04H 1/559* (2013.01); *B29L 2009/00* (2013.01); *B29L 2031/4878* (2013.01); *B32B 2038/0028* (2013.01); *B32B 2250/20* (2013.01); *B32B 2262/0253* (2013.01); *B32B 2262/0292* (2013.01); *B32B 2274/00* (2013.01); *B32B 2307/51* (2013.01); *B32B 2555/02* (2013.01); *Y10T 428/2457* (2015.01)

(58) Field of Classification Search
CPC .... B32B 3/30; B32B 5/02; B32B 5/02; B32B 5/022; B32B 5/04; B32B 7/00; B32B 7/02; B32B 7/08; B32B 37/00; B32B 37/008; B32B 37/008; B32B 37/0084; B32B 37/10; B32B 37/14; B32B 37/14; B32B 37/144; B32B 38/00; B32B 38/001; B32B 38/001; B32B 38/0012; B32B 38/10; B32B 38/18; B32B 38/18; B32B 38/187; B32B 38/187; B32B 38/1875; A61F 13/00; A61F 13/10; A61F 13/15; A61F 13/15; A61F 13/156; A61F 13/156; A61F 13/1569; A61F 13/1569; A61F 13/15699; D04H 1/00; D04H 1/40; D04H 1/43; D04H 1/43; D04H 1/437; D04H 1/437; D04H 1/4374; D04H 1/50; D04H 1/55; D04H 1/55; D04H 1/559
See application file for complete search history.

(56) References Cited

U.S. PATENT DOCUMENTS

| | | | |
|---|---|---|---|
| 2002/0026660 | A1* | 3/2002 | Goda .................... A41D 31/02 2/78.3 |
| 2002/0193774 | A1 | 12/2002 | Otsubo |
| 2006/0169387 | A1 | 8/2006 | Nayar et al. |
| 2009/0035527 | A1* | 2/2009 | Kobayashi ........ A61F 13/15593 428/167 |
| 2014/0102618 | A1* | 4/2014 | Okuda .................... D04H 1/70 156/73.4 |

FOREIGN PATENT DOCUMENTS

| | | |
|---|---|---|
| JP | 2007-022066 A | 2/2007 |
| JP | 2008-148834 A | 7/2008 |
| JP | 2008-526552 A | 7/2008 |
| JP | 5186385 B | 1/2013 |
| WO | WO 2006/115259 A1 | 11/2006 |
| WO | WO 2008/066009 A1 | 6/2008 |

\* cited by examiner (a)

(b)

COMPOSITE SHEET AND METHOD FOR MANUFACTURING THE SAME

RELATED APPLICATION

The present application is a divisional application of U.S. non-provisional patent application Ser. No. 14/397,291, filed Oct. 27, 2014 which is a 35 U.S.C. § 371 national phase filing of International Patent Application No. PCT/JP2013/062338, filed Apr. 26, 2013, through which and to both of which priority is claimed under 35 U.S.C. § 119 to Japanese Patent Application No. 2012-103908, filed Apr. 27, 2012, the complete disclosure of each are hereby expressly incorporated herein by reference.

TECHNICAL FIELD

The present invention relates to composite sheets and, more particularly, to composite sheets being useful as materials for disposable wearing articles such as disposable diapers, disposable toilet-training pants, disposable incontinence pants, disposable sanitary napkins or disposable absorptive pads, and to a method for manufacturing such composite sheets.

BACKGROUND

Conventionally, composite sheets including an elastic sheet and an inelastic sheet are known. For example, Patent Literature 1 discloses a disposable diaper using, as an important constituent, the composite sheet formed from the elastic sheet and the inelastic sheet. The disposable diaper disclosed therein has the elastic sheet on a skin-contact surface and the inelastic sheet on a non-skin-contact surface. The inelastic sheet is bonded to the elastic sheet being under tension so that the inelastic sheet may get many wrinkles. The wrinkles formed in this manner define clearance gaps between the diaper and clothes, ensuring desired breathability.

Conventionally, methods for manufacturing the composite sheet including the elastic sheet and the inelastic sheet are known. For example, Patent Literature 2 discloses a method for manufacturing the composite sheet including a step of joining a nonwoven fabric layer as the inelastic sheet to an elastic base layer as the elastic sheet with use of an ultrasonic system including an anvil and a horn.

CITATION LIST

Patent Literature

{PTL 1}: JP 2008-148834 A
{PTL 2}: JP 2008-526552 A

SUMMARY

Technical Problem

For the composite sheet disclosed in Patent Literature 1, the elastic sheet is flattened. When such a flattened surface is put face-to-face with a wearer's skin, the flattened surface will cling to the wearer's skin and deteriorate the breathability.

The disclosure of the Patent Literature 2 relating to the method for manufacturing the composite sheet describes use of a coextruded elastic film as the elastic base layer but refers to nothing about the elastic fibrous nonwoven fabric.

An object of the present invention is to provide a composite sheet having an elastic layer and an inelastic layer so improved to ensure high breathability and a method for manufacturing such an improved composite sheet.

Solution to Problem

The present invention includes a first aspect and a second aspect.

The first aspect of the present invention relates to an improved composite sheet having a longitudinal direction and a transverse direction being orthogonal thereto and includes an elastic layer defining one surface and being elastically stretchable and contractible at least in the transverse direction and an inelastic layer defining another surface wherein the elastic layer and the inelastic layer are joined to each other, In the composite sheet, the first aspect of the present invention lies in that the elastic layer and the inelastic layer are joined to each other at a plurality of joints spaced from each other in the longitudinal direction as well as in the transverse direction; the elastic layer has a plurality of first linear depressions overlapping the joints and extending in the transverse direction and a plurality of first protrusions being adjacent to the first depressions, respectively, and extending in the transverse direction; and the inelastic layer has a plurality of second depressions overlapping the joints and extending in the longitudinal direction and a plurality of second protrusions being adjacent to the second depressions, respectively, and extending in the longitudinal direction.

The second aspect of the present invention relates to an improved method for manufacturing a composite sheet having a plurality of joints at which an elastic layer and an inelastic layer are joined to each other, first linear depressions formed in the elastic layer so as to overlap the joints, first protrusions formed so as to be respectively adjacent the linear depressions, second protrusions formed in the inelastic layer so as to overlap the joints and second protrusions extending in a direction intersecting with the first protrusions.

In the method for manufacturing the composite sheet, the second aspect of the present invention includes the steps of: conveying an elastic web as material for an elastic layer from a first unwind roller; conveying the elastic web to an ultrasonic system having a sonic horn and an anvil facing the sonic horn via nip rollers; a conveying inelastic web as material for an inelastic layer to the ultrasonic system from second unwind roller; and joining the elastic web and the inelastic web to each other by the ultrasonic system wherein the anvil is provided on a peripheral surface thereof with a plurality of protrusions spaced from each other in a rotating direction as well as in an axial direction so that the elastic web may be conveyed in tight contact with the peripheral surface and a rotating velocity of the anvil is set to be higher than a rotating velocity of the nip rollers.

Advantageous Effects of Invention

According to one or more embodiments of the present invention, the elastic layer is formed with the first protrusions and the first depressions and the inelastic layer is formed with the second protrusions and the second depressions so as to ensure the composite sheet having a high breathability in a planar direction.

DESCRIPTION OF EMBODIMENTS

Figure 1:
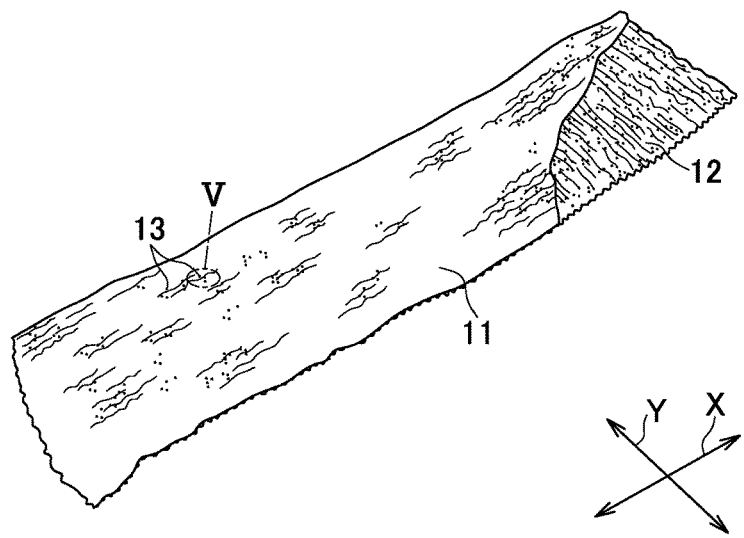
FIG. 1 is a partially cutaway perspective view of a composite sheet according to the present invention as viewed from the side of an elastic layer.
Figure 2:
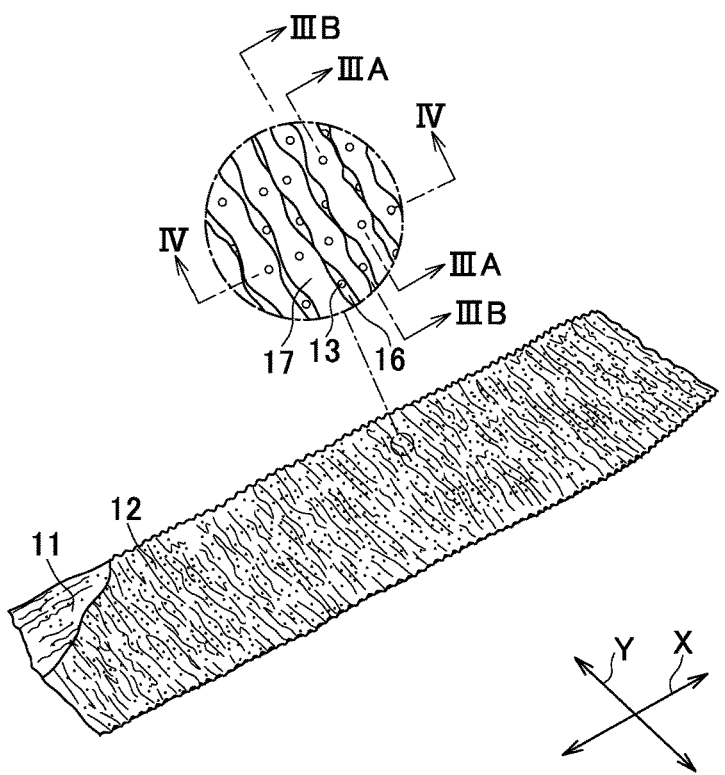
FIG. 2 is a partially cutaway perspective view of the composite sheet as viewed from the side of an inelastic layer.

Referring to FIGS. 1 and 2, a composite sheet 1 has a longitudinal direction Y, a transverse direction X being orthogonal thereto and includes an elastic layer 11 and an inelastic layer 12 joined to each other by many dotted joints 13. The joints 13 may be formed, for example, by subjecting fibers to a sealing treatment with the use of an ultrasonic system.

The elastic layer 11 includes elastic fibers and, according to the present embodiment, the elastic layer 11 is formed of the elastic fibers and the inelastic fibers so that the elastic layer 11 may be elastically expanded and contracted in the transverse direction X. Specifically, the elastic layer 11 has quality of material such that a residual strain read immediately after the elastic layer 11 has been released from its state 100% stretched in the transverse direction X is 30% or less, preferably 20% or less. In FIGS. 1 and 2, the elastic layer 11 of the composite sheet 1 is in a state of contraction released from any stretching force. The elastic layer may be formed from a mixture of the elastic fibers and the inelastic fibers or respective layers may be formed from the respective fibers and then these layers may be layered to form the elastic layer.

The elastic fibers may be formed exclusively of a thermoplastic elastomer or formed from a mixture of the thermoplastic elastomer and other resins. As material for the thermoplastic elastomer, various types of elastomers such as a polystyrene elastomer, polyolefin elastomer, polyurethane elastomer or polyamide elastomer may be selectively used. With respect to a fiber morphology, the elastic fibers may be single-type unsupported fibers or conjugate fibers and, for the conjugate fibers, core-in-sheath type conjugated fibers or side-by-side type conjugated fibers may be used.

The inelastic fibers preferably include thermoplastic resins, particularly polyolefin resins in the form of single-type fibers or mixed fibers including a plurality of polyolefin resins. Further, the inelastic fibers may be in the configuration of core-in-sheath type, side-by-side type, single-type fibers or in the morphology of split fibers. For example, a polyethylene, polypropylene or ethylene-α olefin copolymer may be used as polyolefin resins.

Fiber diameter of the elastic fibers is in a range of about 5 to about 100 μm, preferably in a range of about 10 to about 40 μm and fiber diameter of the inelastic fibers is in a range of about 1 to about 40 mm, preferably in a range of 10 to 30 μm. In fact, the fiber diameter of the inelastic fibers is preferably smaller than the fiber diameter of the elastic fibers.

As material for the inelastic layer 12, various types of fibrous nonwoven fabrics manufactured using various methods, for example, air-through fibrous nonwoven fabrics, point-bond fibrous nonwoven fabrics (heated roller fibrous nonwoven fabrics), spunlace fibrous nonwoven fabrics, spunbond fibrous nonwoven fabrics and meltblown fibrous nonwoven fabrics may be selectively used. Not only the fibrous nonwoven fabrics but also other kinds of materials such as woven fabrics, knitted clothes or resin films may be used.

Figure 3:
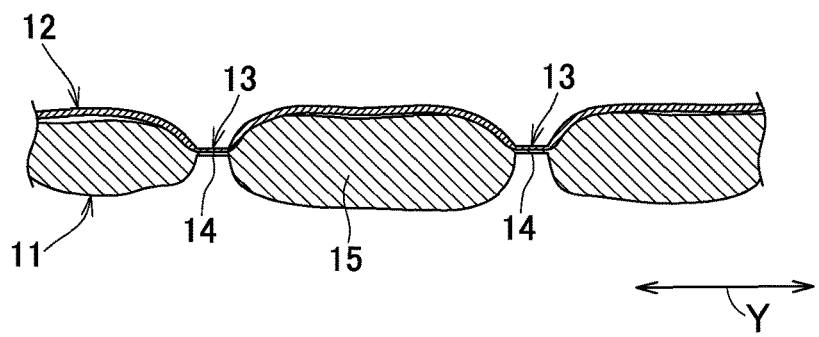
FIG. 3 (a) is a scale-enlarged sectional view taken along line IIIA-IIIA in FIG. 2 and FIG. 3 (b) is a scale-enlarged sectional view taken along line IIIB-IIIB in FIG. 2.
Figure 3:
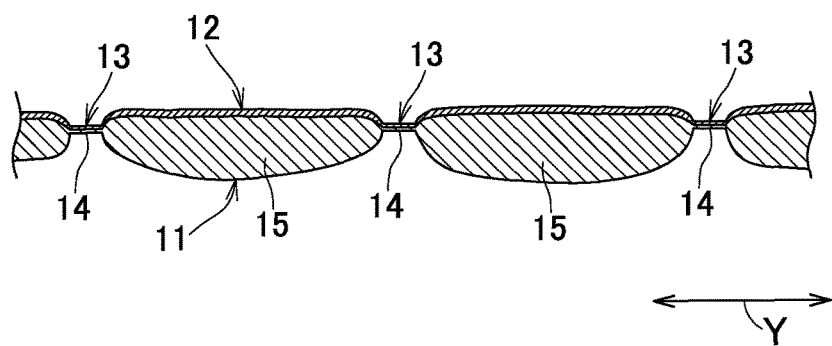
Figure 5:
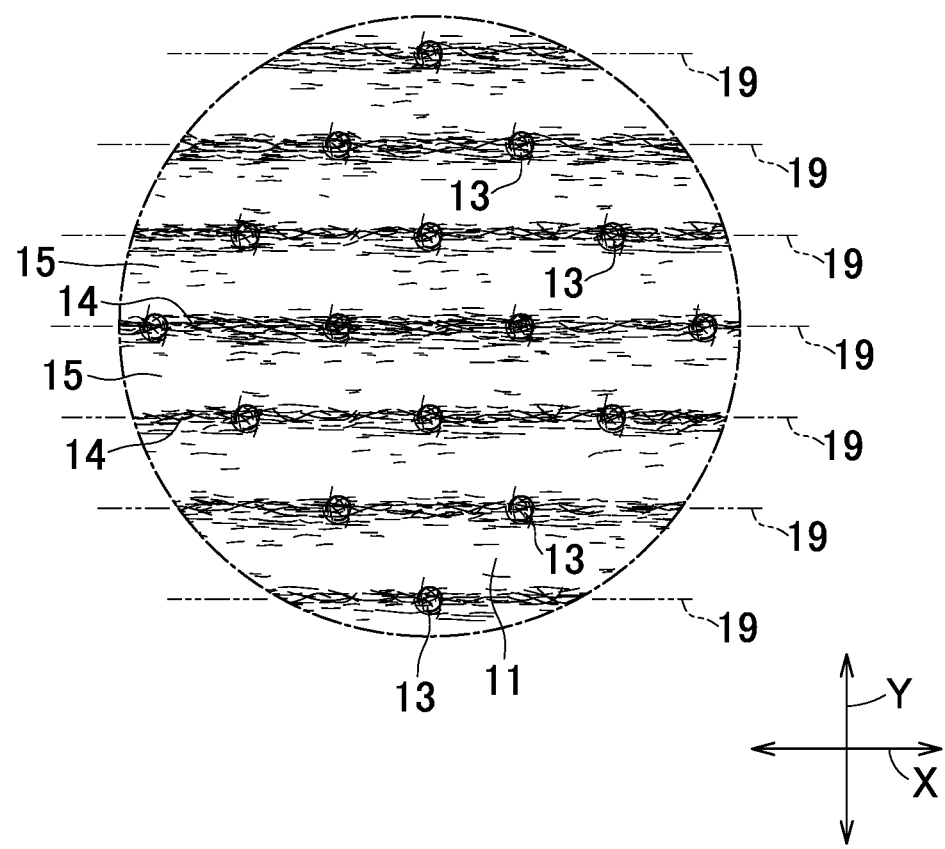
FIG. 5 is a scale-enlarged diagram illustrating an encircled portion V in FIG. 1.

Referring to FIGS. 1, 3 and 5, the elastic layer 11 is formed with a plurality of first depressions 14 overlapping the joints 13 and extending in the transverse direction X and a plurality of first protrusions 15 being adjacent to the first depressions 14 and extending in the transverse direction X. The first protrusions 15 are formed primarily of fibers forming the elastic layer 11. The fibers of the first protrusions 15 are crooked or crimped (not shown) so that the elastic layer 11 as a whole may be stretched in the longitudinal direction Y as well as in the transverse direction X as these fibers are stretched. Particularly, in the transverse direction X, the elastic layer 11 is elastically stretchable and contractible.

Figure 4:
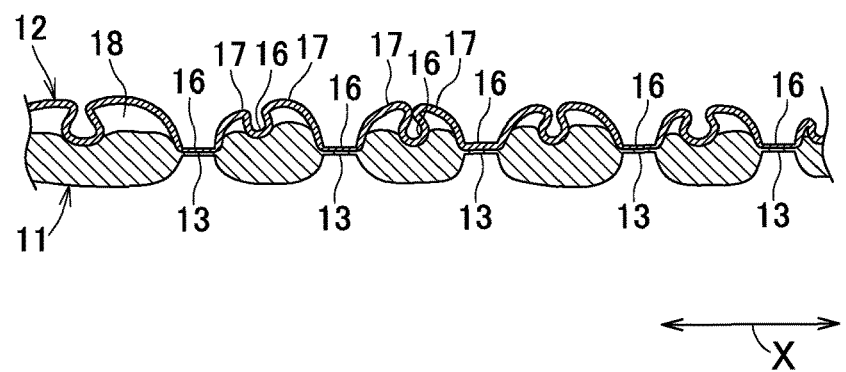
FIG. 4 is a scale-enlarged sectional view taken along line IV-IV in FIG. 2.

Referring to FIGS. 2 and 4, the inelastic layer 12 is formed with a plurality of second depressions 16 overlapping the joints 13 and extending in the longitudinal direction Y and a plurality of second protrusions 17 being adjacent to the second depressions 16 and extending in the longitudinal direction Y. The inelastic layer 12 is bonded at the joints 13 to the elastic layer 11 under tension in the transverse direction X and upon release of the tension, the inelastic layer 12 is formed with the second depressions 16 and the second protrusions 17 both extending in the longitudinal direction Y. Along the second depressions 16, the elastic layer 11 and the inelastic layer 12 are put in contact with each other and, along the second protrusions 17, the inelastic layer 12 is set apart from the elastic layer 11 to define clearance gaps 18 between these sheets. The inelastic layer 12 is approximately inelastic, i.e., not elastically contractible. For this reason, the inelastic layer 12 may be bonded to the elastic layer 11 under tension and then the elastic layer 11 may be released from such tension to ensure that the inelastic layer 12 is loosened between each pair of the adjacent joints 13 and, in consequence, the second protrusions 17 are formed.

Referring to FIG. 5, a plurality of the joints 13 are formed along a plurality of imaginary lines 19 extending in the transverse direction X and distanced from each other in the longitudinal direction Y wherein the joints 13 are distanced from each other in the transverse direction X along each of these imaginary lines 19. In each pair of the adjacent imaginary lines 19, the respective joints 13 are arranged so that these joints 13 are out of alignment with each other in the longitudinal direction Y and arranged in a staggered array. With such arrangement of the joints 13, the elastic layer 11 is formed with the first protrusions 15 extending in the transverse direction X along the respective imaginary lines 19. The inelastic layer 12 is formed with wrinkles intersecting with the imaginary lines 19 and these wrinkles define the second protrusions 17 extending in the longitudinal direction Y.

In the composite sheet 1 described above, the first protrusions 15 of the elastic layer 11 extend in the transverse direction X and the second protrusions 17 of the inelastic layer 12 extend in the longitudinal direction Y so that the first protrusions 15 intersect with the second protrusions 17 so as to ensure a desirable flexibility of the composite sheet 1 in the longitudinal direction Y as well as in the transverse direction X. Assuming, for example, that both the first protrusions 15 and the second protrusions 17 extend in the longitudinal direction Y, the composite sheet 1 will be easily bent along the longitudinal direction Y but not along the transverse direction X. In contrast, these protrusions 15, 17 of the composite sheet 1 according to the present embodiment extend in the directions X, Y intersecting with each other so that the composite sheet 1 may be bent in the longitudinal direction Y as well as in the longitudinal direction X and the composite sheet 1 as a whole may be flexibly bent.

Mass of the composite sheet 1 is in a range of about 50 to about 200 g/m2, preferably in a range of about 70 to about 120 g/m2. The mass was measured pursuant to 5.2 of JIS (Japanese Standards) L 1906.

Thickness was measured with use of THICKNESS GAUGE UF-60 manufactured by DAIEI KAGAKU SEIKI MFG. co., ltd. For the measurement, a circular pressing plate having an area preset to 20 cm was used and a measuring load was preset to 0.3 kPa. The composite sheet 1 has the elastic layer 11 formed with the first protrusions 15 and the inelastic layer 12 formed with the second protrusions 17 so that the thickness of the sheet 1 as a whole is correspondingly increased to provide the relatively bulky composite sheet. Particularly, the first protrusions 15 of the elastic layer 11 are primarily defined by fibers are not apt to be flattened and, even if flattened, an original bulk is restored upon release from a pressure having been put thereupon. Thus, obtained is the composite sheet 1 that is bulky and comfortable in texture.

Stretch ratio in the transverse direction X of the composite sheet 1 is in a range of about 1.0 to about 4.0, preferably in a range of 1.2 to 3.2. The stretch ratio is calculated by dividing a dimension in the transverse direction X of a test piece in its stretched state by a dimension in the transverse dimension X of this test piece in its natural state. The term "stretched state" used herein means the state in which the wrinkles of the inelastic layer 12 as the constituent of the composite sheet 1 have been smoothed out until the second protrusions 17 and the second depressions 16 are approximately flattened and the term "natural state" used herein means a state after the composite sheet 1 has been released from the stretched state and left as it is in atmospheric conditions of 20° C. and 60% RH for an hour or more.

Breathability in planar direction of the composite sheet 1 is in a range of about 60 to about 120 $m^3/m^2/min$, preferably in a range of about 70 to about 110 $m^3/m^2/min$. The breathability in the planar direction was measured with use of KES-F8 Air-Permeability Tester manufactured by KATO TECH CO., LTD. The composite sheet 1 was cut in a size of 100 mm×100 mm as a test piece, then an air shutoff plate was put on the test piece and a breathability was calculated from an air flow resistance of the air passing over the surface of the test piece during supply and removal of air. As the air shutoff plate, an acrylic plate set up to be 0.3 $g/cm^2$ was used.

Figure 6:
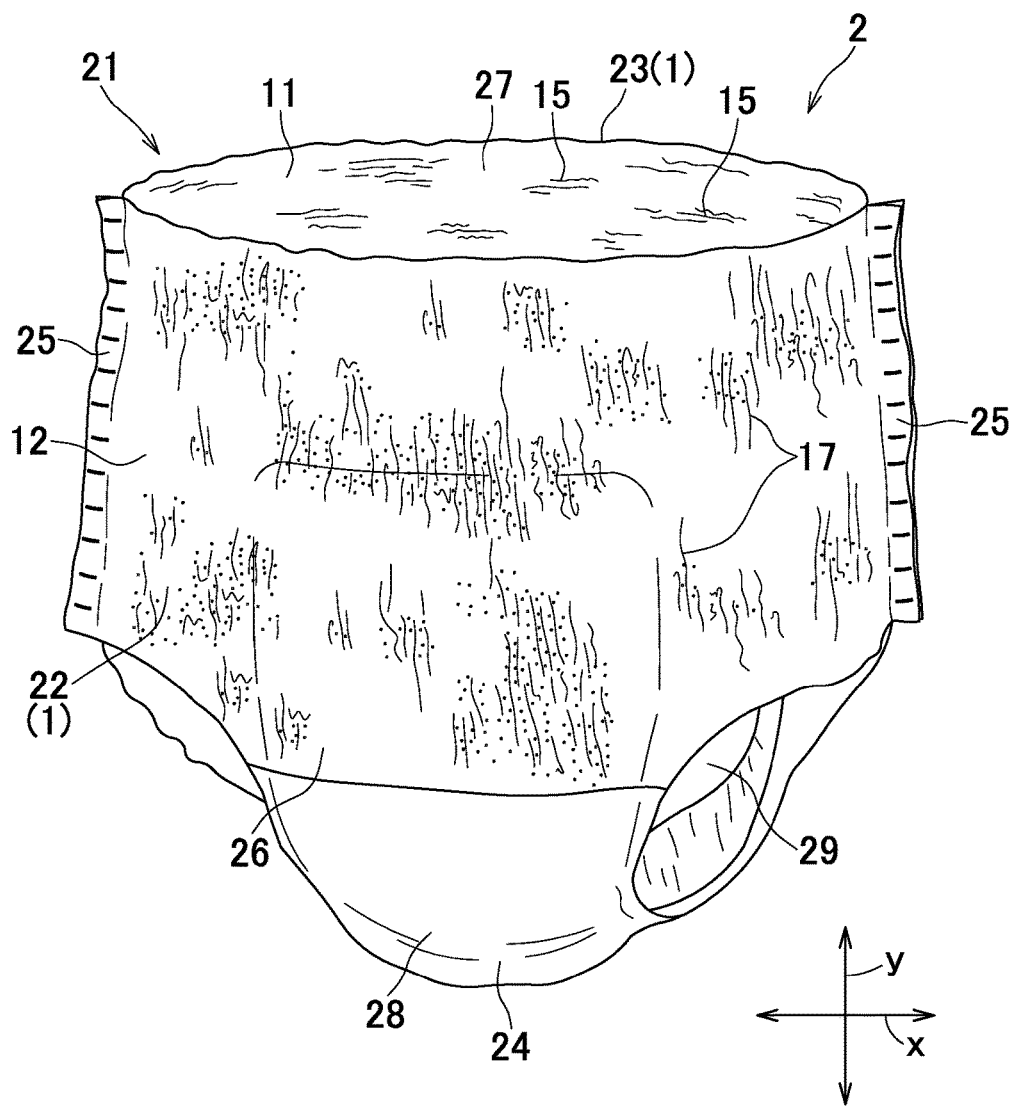
FIG. 6 is a perspective view illustrating a disposable diaper as an example of the disposable wearing article using the composite sheet.

Referring to FIG. 6, the composite sheet 1 as has been described above is useful for a disposable diaper 2 as an example of disposable wearing articles. The disposable diaper 2 has a longitudinal direction y and a transverse direction x being orthogonal thereto and includes a skin-contact surface and a non-skin-contact surface on the other side thereof, a chassis 21 and an absorbent structure 29 allocated on the skin-contact surface of the chassis 21. The chassis 21 has a front waist region 22, a rear waist region 23 and a crotch region 24 extending between the front and rear waist regions 22, 23. Both lateral portions 25 of the chassis 21 are joined to each other along continually extending seams to couple the front and rear waist regions 22, 23 with each other, thereby forming a waist-opening and leg-openings.

The chassis 21 is allocated on the non-skin-contact surface and includes elastic front and rear waist sheets 26, 27 partially defining the front and rear waist regions 22, 23 and the crotch region 24, and an inelastic base sheet 28 adapted to connect the front and rear waist sheets 26, 27 and to primarily define the crotch region 24. The absorbent structure 29 is allocated on the interior side of the front and rear waist sheets 26, 27 and the base sheet 28. The absorbent structure 29 may be prepared by, for example, wrapping a mixture of wood fluff pulp and superabsorbent polymer particles with a liquid-diffusive sheet (not shown).

As the front and rear waist sheets 26, 27 described above, the composite sheet 1 may be used. In the present embodiment, the longitudinal direction Y corresponds to the longitudinal direction y of the diaper and the elastic layer 11 lies on the skin-contact surface. Use of the composite sheet 1 makes it possible to put the chassis 21 in close contact with the wearer's body at least in the front and rear waist regions 22, 23. In addition, the elastic layer 11 of the composite sheet 1 is formed with the first protrusions 15 and the first depressions 14 so that the clearance gaps are formed between the composite sheet 1 and the wearer's skin, and whereby a desired breathability is ensured. The inelastic layer 12 is also formed with the second protrusions 17 and the second depressions 16 so that the clearance gaps are formed also between the composite sheet 1 and the wearer's clothes and whereby a desired breathability is ensured. In this way, the clearance gaps are formed both on the side of the skin-contact surface and the side of the non-skin-contact surface of the diaper 2 so that further improved breathability is maintained.

The first protrusions 15 and the second protrusions 17 extend in two directions intersecting with each other and, in consequence, a sufficient flexibility of the sheet as a whole is maintained to make it possible for the front and rear waist sheets 26, 27 to follow the movement of the wearer, thereby preventing the diaper being displaced during use thereof. When the composite sheet 1 is used in the diaper 2 described above, it is also possible to allocate the elastic layer 11 on the side of the non-skin-contact surface. Even so, it is possible to maintain a desired breathability since both the skin-contact surface and the non-skin-contact surface of the diaper 2 are formed with the wrinkles.

Use of the composite sheet 1 for the front and rear waist sheets 26, 27 in the diaper described above makes it possible to ensure a desired breathability, thereby preventing the diaper 2 from being put in tight contact with the wearer's waist due to moisture, for example, sweat. If the waist sheets is kept in tight contact with the wearer's waist, it would be difficult to put on or to take off the diaper 2 but the diaper 2 according to the present embodiment make it possible to prevent such situation. Further, the sufficient breathability is ensured, and whereby it is possible to prevent skin troubles such as eruption which otherwise might develop on the wearer's skin.

Figure 7:
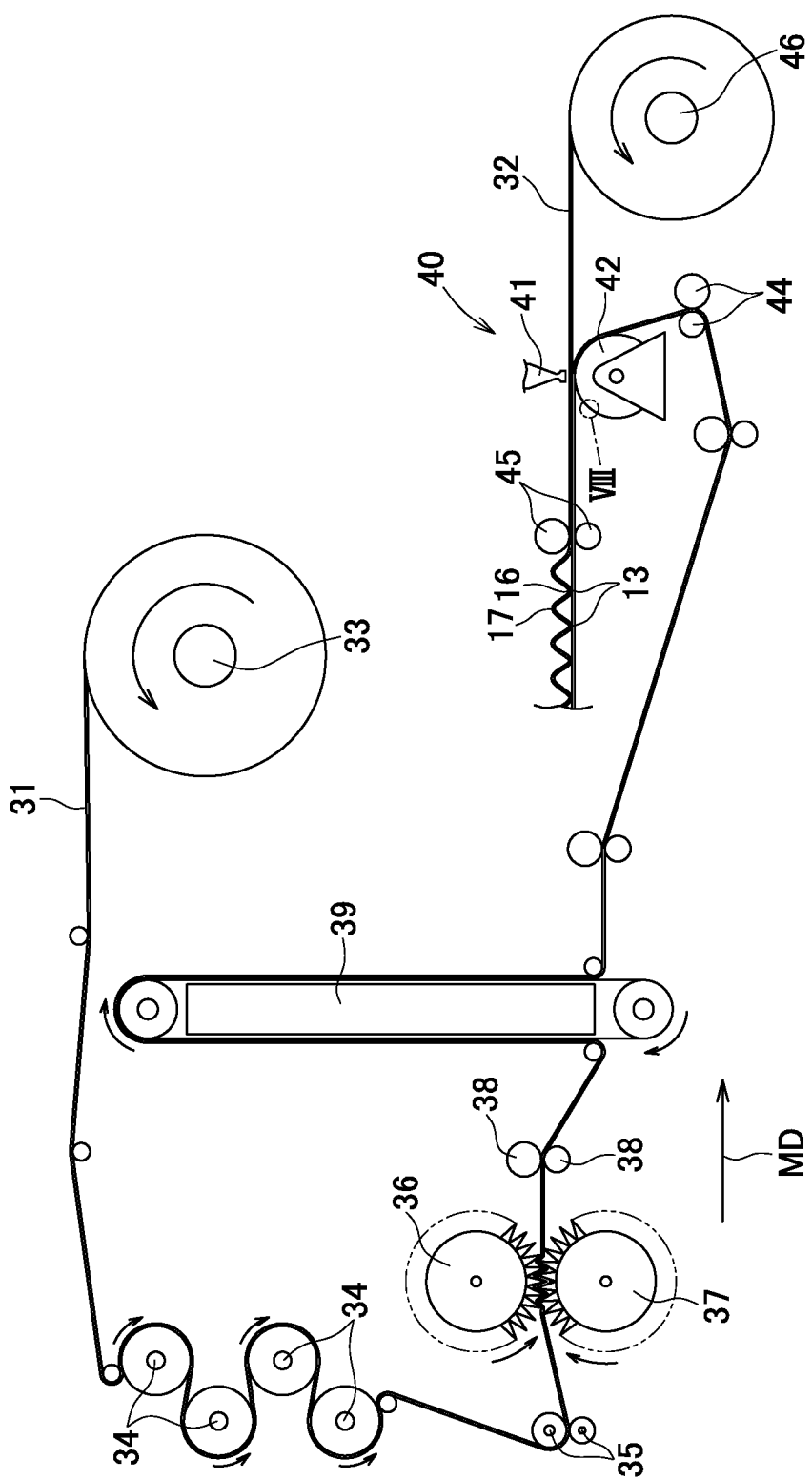
FIG. 7 is a schematic diagram illustrating a process for manufacturing the composite sheet.

The composite sheet 1 as described above may be manufactured by a method schematically illustrated in FIG. 7. The method for manufacturing the composite sheet 1 uses an elastic web 31 corresponding to the elastic layer 11 and an inelastic web 32 corresponding to the inelastic layer 12 as material. As material for the elastic web 31, fibrous nonwoven fabrics formed of, for example, continuous fibers of thermoplastic polyurethane elastomer as elastic fibers and continuous fibers of polypropylene as inelastic fibers may be used. Fiber diameter of the thermoplastic polyurethane elastomer is about 21 mm and fiber diameter of the polypropylene is about 21 mm wherein a content ratio of the thermoplastic polyurethane elastomer is 47% (mass ratio).

The elastic web 31 is conveyed from a first unwind roller 33 at a rate, for example, of about 45.5 m/min. The elastic web 31 conveyed in this manner is heated by a plurality of preheating rollers 34 and further conveyed to a geared stretcher. The preheating rollers 34 are heated at a temperature of about 80° C.

The geared stretcher includes a pair of first nip rollers 35 heated at a temperature of about 80° C., a pair of gear rollers 36, 37 heated at a temperature of about 55° C. and a pair of second nip rollers 38. Velocity of the first nip rollers 35 is about 45.5 m/min and velocity of the second nip rollers 38 is about 54.5 m/min. Specifically, between the first and second nip rollers 35, 38, the elastic web 31 is stretched in a machine direction MD as it passes through the geared rollers 36, 37 under heating. The elastic web 31 stretched in this manner is then conveyed by a cooling conveyor 39 and cooled. Conveying velocity of the cooling conveyor 39 is about 50.0 m/min.

Figure 8:
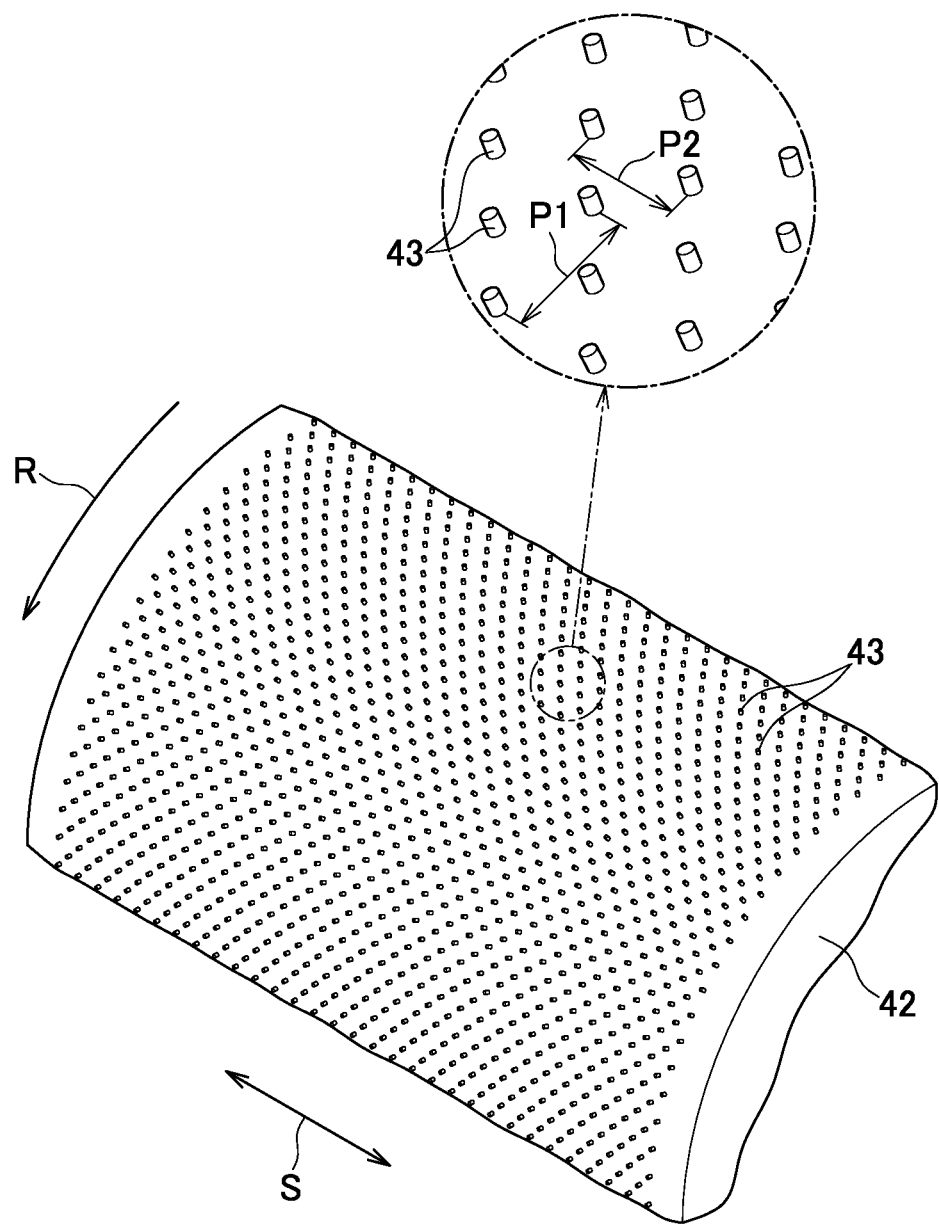
FIG. 8 is a scale enlarged diagram illustrating an encircled portion VIII in FIG. 7.

The elastic web 31 having been stretched in this manner is then conveyed to an ultrasonic system 40. The ultrasonic system 40 includes a sonic horn 41 and a roller-like anvil 42. The anvil 42 is formed on a peripheral surface thereof with a plurality of protrusions 43 arranged so as to define a staggered array. Referring to FIG. 8, each of these protrusions 43 formed on the entire peripheral surface of the anvil 42 has a diameter of about 0.8 mm and a height of about 1.0 mm. A pitch P1 between each pair of the protrusions 43 being adjacent in a rotational direction R is about 6.1 mm and a pitch P2 between each pair of the protrusions 43 being adjacent in an axial direction S is about 6.0 mm. The term "pitch" used herein means a center-to-center dimension of each pair of the adjacent protrusions 43, 43. The elastic web 31 is conveyed in tight contact with the peripheral surface of the anvil 42. Rotating velocity of the anvil 42 is about 100 m/min.

To convey the elastic web 31 further, a pair of third nip rollers 44 is located upstream of the ultrasonic system 40 and a pair of fourth nip rollers 45 is located downstream of the ultrasonic system 40. Velocity of the third nip rollers 44 is about 54.5 m/min and velocity of the fourth nip rollers 45 is about 100 m/min. The elastic web 31 conveyed from the third nip rollers 44 to the fourth nip rollers 45 via the ultrasonic system 40 is stretched in the machine direction MD particularly between the third nip rollers 44 and the anvil 42 under the effect of differential rotating velocity of these nip rollers 44 and anvil 42. Normally, the dimension in the direction intersecting with the machine direction MD is reduced in a manner of necking as the elastic web 31 is stretched in the machine direction MD in such the manner as mentioned above. However, the anvil 42 is formed on its peripheral surface with a plurality of the protrusions 43 according to the present embodiment and the fibers of the elastic web 31 are caught by these protrusions 43, assuring the necking to be restrained.

The inelastic web 32 conveyed from a second unwind roller 46 is laminated on the elastic web 31 conveyed in tight contact with the anvil 42. As material for the inelastic web 32, a fibrous nonwoven fabric including thermoplastic resin, for example, a spunbond fibrous nonwoven fabric of core-in-sheath type using a polypropylene/polyethylene copolymer for the sheath portion and using polypropylene for the core portion may be used. The inelastic web 32 has a mass of about 28.4 g/m2 and a thickness of about 0.31 mm. Velocity of the second unwind roller 46 is about 100 m/min.

The elastic web 31 and the inelastic web 32 now in the laminated state are formed with the joints 13 under the cooperation of the sonic horn 41 and the anvil 42. Specifically, the thermoplastic synthetic resin in the elastic web 31 and the inelastic web 32 are welded and joined together. Frequency and pressure of the sonic horn 41 are set to about 20 KHz and 300 N/160 mm, respectively.

The laminate of the elastic web 31 and the inelastic web 32 having been formed with the joints 13 in the manner as described above is released from a stretched state of the elastic web 31 after the laminate has passed through the fourth nip rollers 45. Upon release from the stretched state, the elastic web 31 contracts in the machine direction MD and, in consequence, the inelastic web 32 slacks between each pair of the adjacent joints 13 to get wrinkles which define the second protrusions 17 extending in a direction intersecting with the machine direction MD. At the joints 13 formed in this manner, the inelastic web 32 is joined to the elastic web 31 so as to define the second depressions 16 (See FIGS. 2 and 4).

When released from a stretched state, the elastic web 31 is released also from a state of the introflextion in the cross direction and the dimension thereof in the cross direction. Specifically, the fibers of the elastic web 31 extending at random in the machine direction MD and in the cross direction before the elastic web 31 is stretched in the machine direction MD are now stretched between the third and fourth nip rollers 44, 45 so as to be oriented along the machine direction MD. Consequently, the elastic web 31 extends in the machine direction MD and has its dimension in the cross direction reduced. When the elastic web 31 is released from such stretched state, most of the fibers having been oriented in the machine direction MD at least partially restore the original state thereof, gather in a thickness direction and become bulky. The portions of the elastic web 31 having gathered so as to become bulky define the first protrusions 15 and the portions of the elastic web 31 corresponding to the respective joints 13 define the first depressions 14 since it is impossible for these portions to become bulky (See FIGS. 1, 3 and 5). Formation of the joints 13 makes it possible to form the bulky first protrusions 15 in which a fiber density is sufficiently low to improve further the breathability in planar direction.

Table 1 shows the other embodiments of the composite sheet 1 manufactured by the equipment basically as has been described above. In Table 1, Embodiment 1 is the composite sheet 1 under the conditions exactly as have been described above and Embodiments 2 through 6 are composite sheets 1 manufactured with use of the same apparatus but the monitor configurations thereof varied from that adopted in Embodiment 1. Table 1 lists characteristics of the elastic web 31 and characteristics of the composite sheet 1 manufactured from the composite sheet 1 in the respective embodiments and the comparative example.

"Stretch ratio" in the Table corresponds to the stretch ratio in the paragraph [0024] of the specification. In any one of Embodiments 1 through 6, it is possible to obtain the composite sheet 1 having the desirable stretch ratio and breathability in the planar direction.

For Comparative Example, the elastic web 31 and the inelastic web 32 were bonded to each other with use of hot melt adhesive instead of welding the elastic web 31 and the inelastic web 32 to each other with use of the ultrasonic system. As the hot melt adhesive, hot melt adhesive containing a polystyrene elastomer was used and the inelastic web 32 is coated with such hot melt adhesive with use of a curtain coater at a nozzle pitch of 5 mm and in a mass of 2 g/m2. The monitor configuration for Comparative Example was same as for Embodiment 1. Compared to the composite sheet according to Embodiments, the breathability in the planar direction was relatively low in the composite sheet according to Comparative Example probably due to the absence of the first and second protrusions. Though not listed in Table 1, a bonding strength between the elastic web 31 and the inelastic web 32 is lower than those in Embodiments and in a range of about 40% of that in Embodiment 1.

unacceptably decrease the area over which the elastic layer 11 is joined to the inelastic layer 12 and the elastic layer 11 and the inelastic layer 12 will be readily peeled off from each other. The cross-sectional area of 10 mm2 or more will often make the joints 13 filmy, unacceptably enlarge the area over which the elastic layer 11 is joined to the inelastic layer 12 so as to deteriorate feel against the wearer's skin. The pitches P1, P2 of the protrusions 43 are preferably in a range of about 1 to about 20 mm. The pitches P1, P2 of 1 mm or less, it will be difficult to form the elastic layer 12 with the second protrusions 17 and the pitches P1, P2 of 20 mm or more will cause an anxiety that the thickness of the composite sheet 1 might unacceptably increase. A height dimen-

TABLE 1

| | | | Emb. 1 | Emb. 2 | Emb. 3 | Emb. 4 | Emb. 5 | Emb. 6 | Comparative Example |
|---|---|---|---|---|---|---|---|---|---|
| Monitor configuration | Velocity of 1st unwind roller (V1) | (m/min) | 45.5 | 45.5 | 45.5 | 66.7 | 50.0 | 41.7 | 45.5 |
| | Velocity of 2nd unwind roller (V2) | (m/min) | 100.0 | 100.0 | 100.0 | 100.0 | 100.0 | 100.0 | 100.0 |
| | Velocity ratio (V2/V1) | (multiple) | 2.2 | 2.2 | 2.2 | 1.5 | 2.0 | 2.4 | 2.2 |
| | Velocity of cooling conveyor | (m/min) | 50.0 | 50.0 | 50.0 | 73.3 | 55.0 | 45.8 | 50.0 |
| | Velocity of 3rd conveying roller | (m/min) | 54.5 | 72.7 | 100.0 | 80.0 | 60.0 | 50.0 | 54.5 |
| | Velocity of anvil | (m/min) | 100.0 | 100.0 | 100.0 | 100.0 | 100.0 | 100.0 | 100.0 |
| Elastic web | Length of cross-direction on 1st unwind roller | (mm) | 150 | 150 | 150 | 150 | 150 | 150 | 150 |
| | Length of cross-direction on anvil | (mm) | 93 | 83 | 67 | 110 | 95 | 95 | 90 |
| | Percentage of maintaining width | (%) | 62.0 | 55.3 | 44.7 | 73.3 | 63.3 | 63.3 | 60.0 |
| Composite sheet | Mass | (g/m$^2$) | 101.0 | 108.5 | 120.0 | 78.4 | 91.5 | 105.6 | 100.3 |
| | Thickness | (mm) | 2.89 | 3.04 | 3.08 | 2.33 | 2.82 | 2.92 | 2.57 |
| | Stretch ratio | (multiple) | 2.03 | 2.04 | 2.03 | 1.40 | 1.87 | 2.23 | 1.97 |
| | Breathability in planar direction | (m$^3$/m$^2$/min) | 101 | 80 | 72 | 86 | 96 | 108 | 41 |

If the anvil 42 is not formed with the protrusions 43 in the manufacturing method as described above, necking of the stretched elastic web 31 will become remarkable. The remarkable necking of the elastic web 31 will thicken particularly both lateral portions of the elastic web 31 and increase a thickness unevenness relative to the interior portion. If the elastic web 31 in such condition is joined to the inelastic web 32, there is a high possibility that a bonding strength might be unacceptably poor in the thickened portions and might be excessively high in the thin portions. In consequence, the bonding strength might be uneven during forming the joints. According to the present invention, in view of this, the anvil 42 is formed with the protrusions 43 to restrain the necking, thereby restricting the unevenness in the strength of the joints.

Meanwhile, a certain degree of the necking appearing in the elastic web 31 is necessary to form the elastic web 31 with the first protrusions 15. In view of this, the protrusions 43 of the anvil 42 are not for the purpose of completely preventing occurrence of the necking but for the purpose of controlling the necking so that the unevenness in the bonding strength of the joints may be appropriately restricted.

While the joints 13 are formed with use of the ultrasonic system 40 according to the present embodiment, it is also possible to form them with use of heat-sealing technique such as an embossing. However, here, the elastic web or the inelastic web as a whole is heated during forming the joints and, consequently, the sheet is apt to be damaged due to heat and, in addition, not easily becomes bulky.

While the protrusions 43 in the ultrasonic system 40 are circular according to the present embodiment, the shape of the individual protrusions 43 is not limited to such circular shape but the other shapes such as rhombic, oval and rectangular shaped may be used. A cross-sectional area thereof is preferably in a range of about 0.1 to about 10 mm2. The cross-sectional area of 0.1 mm2 or less will sion of the protrusion 43 may be in a range of about 0.1 to about 2.0 mm, preferably in a range of about 0.2 to about 1.0 mm. Normally, the thickness of fibrous nonwoven fabric is in a range of about 0.3 to about 2.0 mm so that such fibrous nonwoven fabric may be reliably formed with the joints 13. While the protrusions 43 are arranged in the staggered array according to the present embodiment but not limited to the staggered array. In this regard, in order to control the nicking of the elastic web 31 in the cross direction, it is desired to arrange a plurality of the protrusions 43 spaced from each other in the rotational direction of the anvil 42.

While the elastic web 31 is subjected to geared stretching treatment according to the present embodiment, this is not essential for the present invention. However, the elastic web 31 including the elastic fibers and the inelastic fibers may be subjected to such geared stretching treatment to assure that the inelastic fibers may be stretched, a Young's modulus in a stretched state of the elastic web 31 (elastic layer 11) may be lowered and a flexible texture may be obtained. According to the present embodiment, a gear pitch of the gear rollers 36, 37 is in a range of about 1 to about 10 mm, preferably in a range of about 2 to about 6 mm. The gear pitch of 1 mm or less makes it necessary to reduce the thickness of the respective teeth and, in consequence, the web might be cut by the tooth. The gear pitch of 10 mm or more causes an anxiety that a stretch ratio might be too lowered to ensure the desirable elasticity. An engagement depth of the gears may be adjusted to be about 0.5 mm or more. The engagement depth less than about 0.5 mm may result in an insufficient stretchability of the web. A stretch ratio of the web before and after the step of stretching treatment may set to a range of about 30 to about 400%, preferably in a range of about 50 to about 200%. The stretch ratio of 30% or less makes it difficult to stretch the web and the stretch ratio of 400% or more causes a possibility that the stretched web fiber might be cut and drop off.

The disclosure relating to the present invention described above may be arranged at least as follows.

The composite sheet 1 according to the first aspect of the present invention had the longitudinal direction Y and the transverse direction X being orthogonal thereto, and includes the elastic layer 11 defining one surface and being elastically stretchable and contractible at least in the transverse direction X and the inelastic layer 12 defining the other surface wherein the elastic layer 11 and the inelastic layer 12 are joined to each other, In such composite sheet 1, the first aspect of the present invention includes the following features.

The elastic layer 11 and the inelastic layer 12 are joined to each other at a plurality of joints 13 spaced from each other in the longitudinal direction Y as well as in the transverse direction X.

The elastic layer 11 has the plurality of first depressions 14 overlapping the joints 13 and extending in the transverse direction X and the plurality of first protrusions 15 being adjacent to the first depressions 14, respectively, and extending in the transverse direction X The inelastic layer 12 has the plurality of second depressions 16 overlapping the joints 13 and extending in the longitudinal direction Y and the plurality of second protrusions 17 being adjacent to the second depressions 16, respectively, and extending in the longitudinal direction Y.

The first aspect of the present invention described just above may include at least the following embodiments.

(1) The elastic layer 11 and the inelastic layer 12 are respectively formed of a fibrous nonwoven fabric containing a thermoplastic resin and the elastic layer 11 and the inelastic layer 12 are welded to each other at the joints 13.

(2) The elastic layer 11 includes elastic fibers and inelastic fibers.

(3) At the second protrusions 17, the inelastic layer 12 is spaced from the elastic layer 11 to form clearance gaps 18 therebetween.

(4) The elastic layer 11 is at least partially put in contact with the inelastic layer 12 at the first protrusions 15.

(5) The plurality of the joints 13 are arranged so that these joints 13 are distanced from each other in the transverse direction X along each of imaginary lines 19 extending in the transverse direction X and the joints 13 arranged on each pair of the adjacent imaginary lines 19 are out of alignment in the longitudinal direction Y.

(6) In a wearing article including the skin-contact surface and the non-skin-contact surface opposite thereto for the article wearer and the chassis 21 having front and rear waist regions 22, 23 and the crotch region 24, at least one of the front and rear waist regions is formed of the composite sheet.

The second aspect of the present invention relates to the method for manufacturing a composite sheet 1 having the plurality of joints 13 at which the elastic layer 11 and the inelastic layer 12 are joined to each other, the first depressions 14 formed in the elastic layer 11 so as to overlap the joints 13, the first protrusions 15 formed so as to be respectively adjacent to the first depressions 14, second protrusions 17 formed in the inelastic layer 12 so as to overlap the joints 13 and second protrusions 17 extending in the direction intersecting with the first protrusions 15.

In the method for the composite sheet 1 as has been described just above, the second aspect of the present invention includes the steps of:

the conveying elastic web 31 as material for the elastic layer 11 from the first unwind roller 33;

conveying the elastic web 31 to the ultrasonic system 40 having the sonic horn 41 and the anvil 42 facing the sonic horn 41 via the nip rollers 44;

The conveying inelastic web 31 as material for the inelastic layer 12 to the ultrasonic system 40 from the second unwind roller 46; and joining the elastic web 31 and the inelastic web 32 to each other by the ultrasonic system 40 wherein the anvil 42 is provided on the peripheral surface thereof with the plurality of protrusions 43 spaced from each other in the rotating direction as well as in the axial direction so that the elastic web 31 may be conveyed in tight contact with the peripheral surface and the rotating velocity of the anvil 42 is set to be higher than the rotating velocity of the nip rollers 44.

The second aspect of the present invention described just above may include embodiments at least as described below.
(1) Between the anvil 42 and the nip rollers 44, the elastic web 31 is stretched in the machine direction MD so that the dimension of the elastic web 31 in the cross direction being orthogonal to the machine direction MD after having been stretched is smaller than such dimension before stretching.
(2) The method further including the step of stretching the elastic web 31 by the pair of gear rollers 36, 37 and the elastic web 31 having been stretched in this step is formed with the joints 13.

Terms "first", "second", "third" and "four" used in the specification and Claims of the present invention are used merely to distinguish the similar elements, similar positions or the other similar means.

REFERENCE SIGNS LIST 1 composite sheet
11 elastic layer
12 inelastic layer
13 joints
14 first depressions
15 first protrusions
16 second depressions
17 second protrusions
18 clearance gaps
31 elastic web
32 inelastic web
33 first unwind roller
36 gear roller
37 gear roller
40 ultrasonic system
41 sonic horn
42 anvil
43 protrusions
44 nip rollers
46 second unwind roller

The invention claimed is:
1. A method for manufacturing a composite sheet having a plurality of joints at which an elastic layer and an inelastic layer are joined to each other, first depressions formed in the elastic layer so as to overlap the joints, first protrusions formed so as to be respectively adjacent the first depressions, second protrusions formed in the inelastic layer so as to overlap the joints and second protrusions extending in a direction intersecting with the first protrusions, including the steps of:

conveying an elastic web as material for the elastic layer from a first unwind roller;

conveying the elastic web to an ultrasonic system having a sonic horn and an anvil facing the sonic horn via nip rollers;

conveying inelastic web as material for the inelastic layer to the ultrasonic system from second unwind roller; and joining the elastic web and the inelastic web to each other by the ultrasonic system wherein the anvil is provided on a peripheral surface thereof with a plurality of protrusions spaced from each other in a rotating direction as well as in an axial direction so that the elastic web is conveyed in tight contact with the peripheral surface and a rotating velocity of the anvil is set to be higher than a rotating velocity of the nip rollers.

2. The method according to claim 1 wherein, between the anvil and the nip rollers, the elastic web is stretched in a machine direction so that a dimension of the elastic web in a cross direction being orthogonal to the machine direction after having been stretched is smaller than such dimension before stretching.

3. The method according to claim 1, further including a step of stretching the elastic web by a pair of gear rollers and the elastic web having been stretched in this step is formed with the joints.

* * * * *